(12) United States Patent
Erickson et al.

(10) Patent No.: US 7,516,844 B2
(45) Date of Patent: Apr. 14, 2009

(54) SHARPS CONTAINER FOR USED PEN NEEDLE ASSEMBLIES

(75) Inventors: Thomas E. Erickson, Crosslake, MN (US); James J Erickson, Mound, MN (US); Timothy A. Bachman, Saint Paul, MN (US)

(73) Assignee: Ultimed, Inc., St. Paul, MN (US)

( * ) Notice: Subject to any disclaimer, the term of this patent is extended or adjusted under 35 U.S.C. 154(b) by 263 days.

(21) Appl. No.: 10/862,544

(22) Filed: Jun. 7, 2004

(65) Prior Publication Data

US 2005/0269320 A1 Dec. 8, 2005

(51) Int. Cl.
*B65D 83/10* (2006.01)
(52) U.S. Cl. .................................... 206/366; 206/365
(58) Field of Classification Search ............... 206/364, 206/365, 366, 571, 732, 438, 370; 220/521, 220/908, 810
See application file for complete search history.

(56) References Cited

U.S. PATENT DOCUMENTS

| | | | | |
|---|---|---|---|---|
| 1,333,051 A * | 3/1920 | Young | ...................... | 220/252 |
| 2,326,886 A * | 8/1943 | Rathbun | .................... | 220/252 |
| 2,986,328 A * | 5/1961 | Delas | ....................... | 232/43.1 |
| 4,779,728 A * | 10/1988 | Hanifl et al. | ................ | 206/366 |
| 4,828,107 A * | 5/1989 | Spencer | ..................... | 206/366 |
| 4,890,733 A * | 1/1990 | Anderson | .................. | 206/365 |
| 5,046,614 A * | 9/1991 | Torres et al. | ................. | 206/366 |
| 5,076,429 A * | 12/1991 | Patrick et al. | .............. | 206/370 |
| 5,240,108 A * | 8/1993 | Tonna | ........................ | 206/366 |
| 5,346,086 A * | 9/1994 | Harris | ..................... | 220/254.5 |
| 5,409,113 A | 4/1995 | Richardson et al. | | |
| 5,413,243 A * | 5/1995 | Bemis et al. | ................ | 220/481 |
| 5,494,158 A | 2/1996 | Erickson | | |
| 5,545,145 A | 8/1996 | Clinton et al. | | |
| 5,971,966 A | 10/1999 | Lav | | |
| 6,685,017 B2 | 2/2004 | Erickson | | |
| 2003/0132129 A1 * | 7/2003 | Erickson | ..................... | 206/366 |
| 2003/0168367 A1 | 9/2003 | Pike | | |

* cited by examiner

*Primary Examiner*—Mickey Yu
*Assistant Examiner*—Steven A. Reynolds
(74) *Attorney, Agent, or Firm*—Crompton, Seager & Tufte LLC

(57) ABSTRACT

A sharps container for pen needle assemblies includes an open top-type receptacle, a cover and a manually movable means. The manually movable means is rotatably positioned on the cover and has portions collectively forming a cup-like means for receiving a used pen needle assembly when the manually movable means is in an open position. When the manually movable means is in a closed position, the used pen needle assembly is transferred by gravity to the bottom of the receptacle.

13 Claims, 5 Drawing Sheets

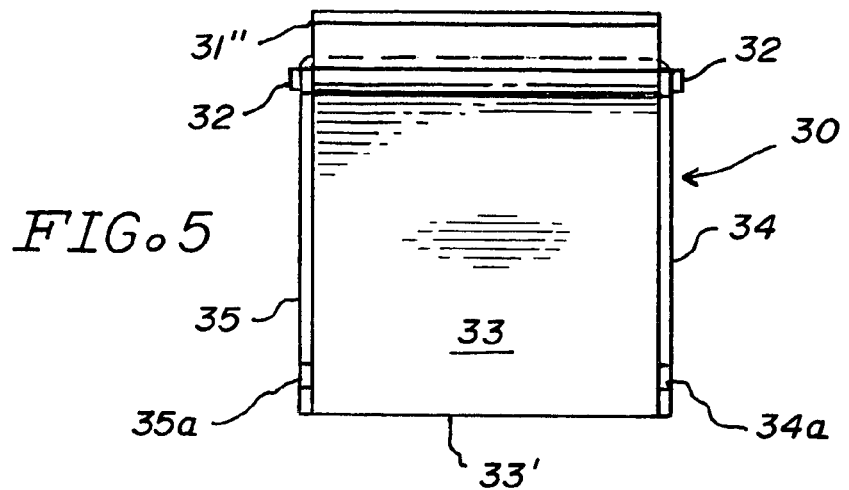
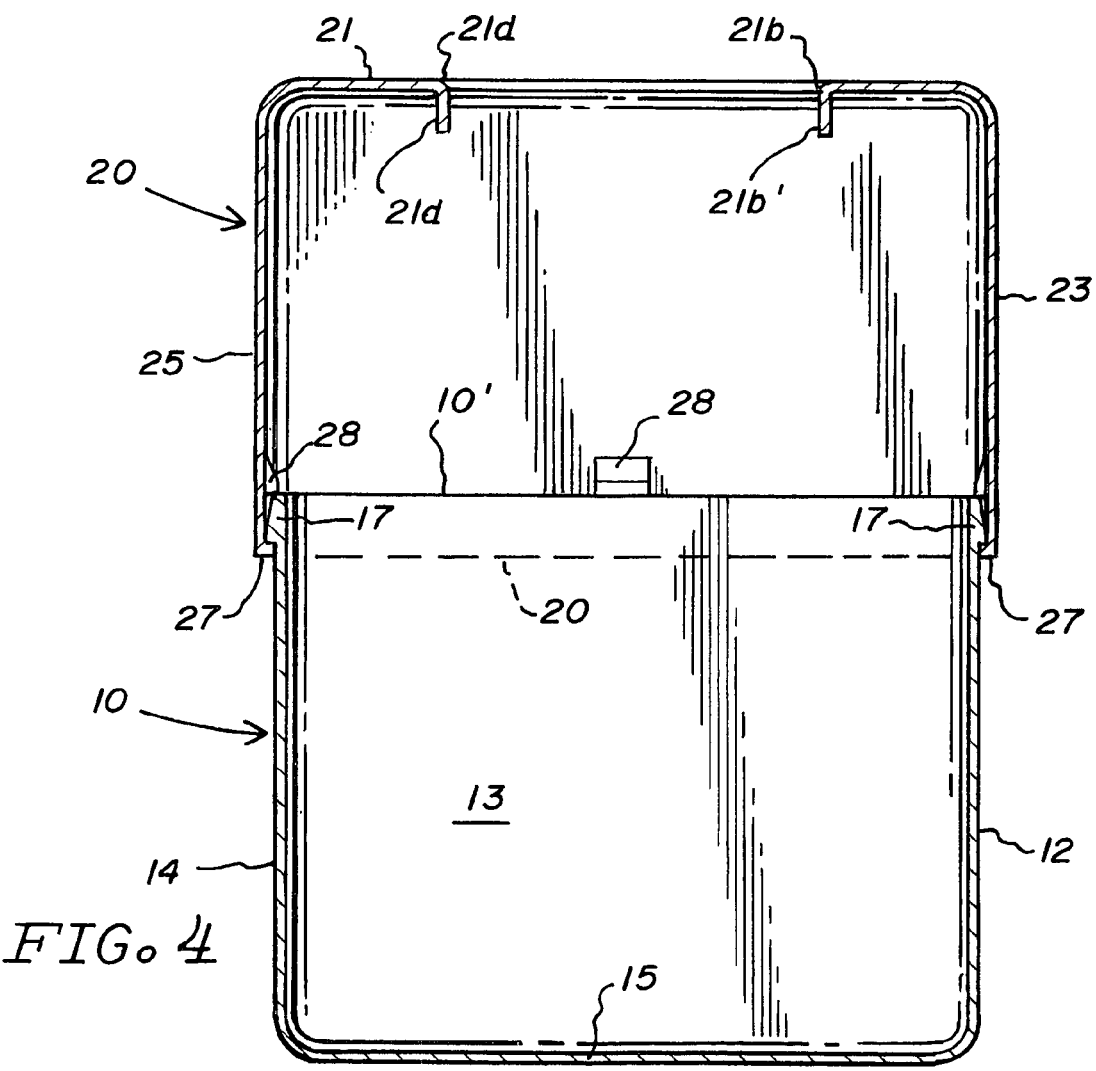

SHARPS CONTAINER FOR USED PEN NEEDLE ASSEMBLIES

BACKGROUND AND FIELD OF THE INVENTION

This invention relates specifically to the safe storage of pen needle assemblies (sometimes referred to herein as PNAs). Because of well known health issues, the safe disposal of medical/other syringes has long been a high priority for the related professions and industries. The prior art containers for such syringes are commonly termed "sharps containers" and many configuration of these are found in public venues such as hospitals, medical clinics, and retail establishments. These containers are usually securely attached to some base means and have a lock means to permit controlled and safe removal of used "sharps."

Medical delivery pens have, more recently, become widely used, e.g., by diabetics, who frequently inject themselves several times a day with accurately measured amounts of insulin or other medication. Medical delivery pens include a reservoir of medication and a distal end adapted to be attached (usually by thread means) to a pen needle assembly. As is well known, the pen needle assembly has (within an outer, generally cylindrical shield) a generally cylindrical housing within which is mounted an axially extending hollow needle, (i) the proximal end of which punctures a seal in the distal end of the medical delivery pen (to allow the flow there-through of medication) when the delivery pen is screwed into the proximal end of the pen needle housing, and (ii) the distal end of which is for insertion into tissue of the person requiring the medication. The pen needle assemblies typically include a removable seal covering the proximal (large diameter) end of the said outer shield and a removable tube-like shield covering the distal portion of the hollow needle. The assembled pen needle assembly is then factory sterilized. The user of a pen needle assembly removes the seal from the outer shield, screws the pen into the proximal end of the pen needle housing, removes the outer and tube-like shields, sets the medical delivery pen for the desired dose of medication, and then inserts the distal end of the pen needle into the target tissue following which the medical delivery pen is actuated to deliver the desired dose of medication through the hollow needle into said tissue.

In a perfect world, the user of a pen needle assembly would, after the first use of a pen needle assembly, carefully detach the used pen needle assembly from the medical delivery pen and safely dispose said assembly. The approved procedure is (i) insertion of the distal end of the needle into the tube-like shield and thence the shielded needle and cylindrical housing into the outer shield, (ii) unscrewing of the medical delivery pen from the proximal end of the pen needle housing, and (iii) placement of the used pen needle assembly into a safe sharps container. Alas, the recommended procedure is not always followed. Used (and potentially dangerous) pen needles, with or without outer shields, are routinely left in unsafe places where third parties may unwittingly be "stuck." Examples of such unsafe places are purses, the seat pockets on the back of aircraft seats, private and public wastebaskets, garbage cans, dumpsters and empty milk bottles or other unsafe containers.

One prior art example of a container for used pen needle assemblies is U.S. Pat. No. 5,545,145 which shows a tube containing a small number of unused pen needle assemblies arranged in axial alignment. This patent also teaches that, as unused assemblies are removed from one end of the tube, then a used assembly may be inserted into the tube from the other end. The tube is adapted to be attached to the side of a medical delivery pen. This arrangement has certain shortcomings. The capacity is quite limited and, potentially dangerous "sticks" could occur when a user tries to insert a used assembly (without the protective outer shield) into the used end of the tube.

Other prior art sharps containers may be used for disposal of used pen needle assemblies; however they are typically far too large and bulky and have other disadvantages.

SUMMARY OF THE INVENTION

The present invention provides a safe, space efficient container for storing a large number of used pen needle assemblies. The invention provides a container which is especially useful for an individual such as a diabetic who may require several daily doses of medication, which doses are during the day (frequently at meal time) and thus may be at the users residence as well as at other locations such as the user's place of work, at a restaurant, in an automobile or aircraft, etc.

In broad terms the present invention provides a container comprising an open-topped receptacle, a cover member, and a manually movable means which may manually rotated from a "closed" position to an "open" position. In the open position the manually movable means may receive a used pen needle assembly. Then manual rotation of the movable means to the closed position facilitates the discharge of the used pen needle assembly into the receptacle. The receptacle is sized to hold a plurality of used pen needle assemblies (with or without the outer shields). The receptacle is a cup-like vessel which, although of a size to hold a large number of used pen needle assemblies, may at the same time be "small" and/or "thin" enough to be conveniently portable for travel with the user.

The cover member is sized to fully cover the open-topped receptacle and has a top surface and a side surface(s).

The manually movable means, in the preferred embodiment, is a rotatable hatch means. The rotatable hatch means is adapted to be mounted in an opening in the top of the cover for rotation between a closed position and an open position. The hatch means includes a top portion, a bottom portion, and a pair of axially spaced-apart side portions which collectively define a cup-like receiving means for only a single pen needle assembly when the hatch means is in the open position.

The cover member includes a baffle means which, in the preferred embodiment, has a curved cross-section. The hatch means is rotatably mounted on the cover. The side portions thereof have curved edges matched to mate with the curved surface of the baffle means when the hatch means is in the open position; in this position the bottom portion of the hatch means and the said side portions effectively block or prevent any "removal" from the receptacle of a previously disposed used pen needle assembly.

The use of the container by the user is easy. The hatch means is manually opened, the used pen needle assembly is placed or dropped into the cup-like receiving means of the hatch means, and then the hatch means is manually rotated to the closed position. When the hatch means is closed, then the used pen needle assembly falls into the receptacle.

BRIEF DESCRIPTION OF THE DRAWINGS

FIG. 4 is a cross-sectional view of the receptacle and cover member as viewed along section lines 4-4 of FIG. 2.

FIG. 5 is a view of the hatch means as viewed along section lines 5-5 of FIG. 3.

DETAILED DESCRIPTION OF THE INVENTION

Figure 1:
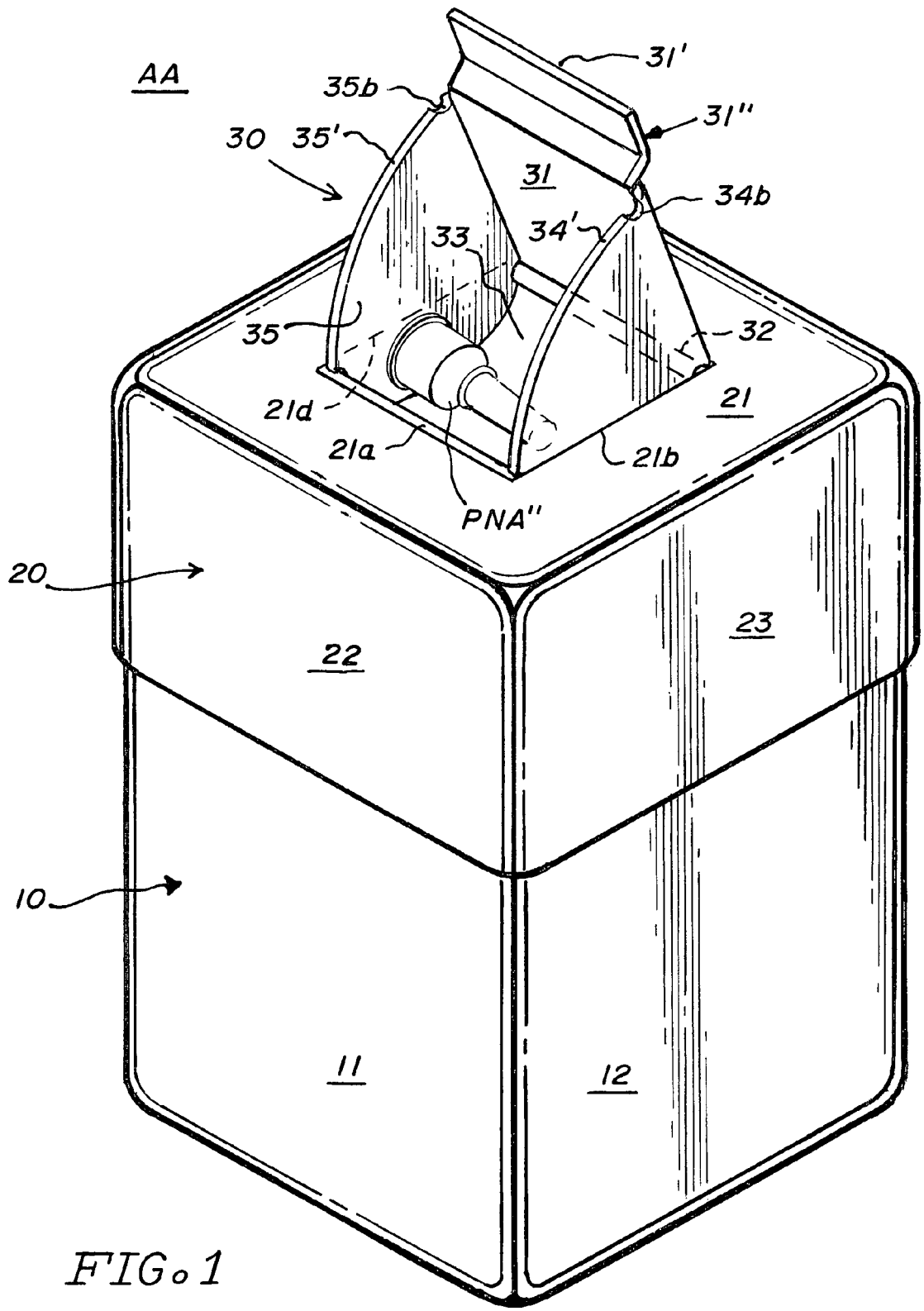
FIG. 1 is an isometric view of a preferred embodiment of a sharps container provided by the invention.
Figure 6:
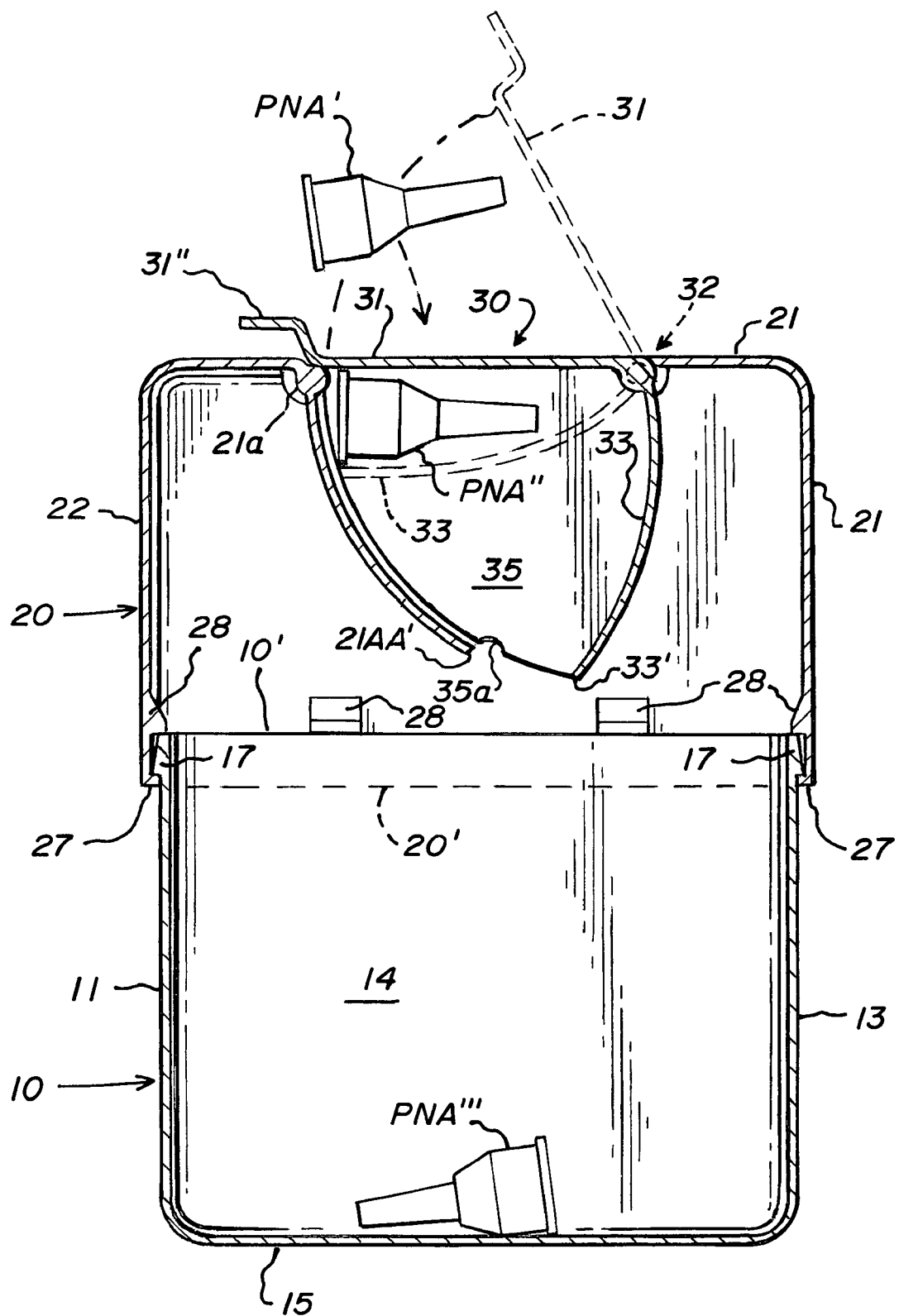
FIG. 6 is a cross-sectional view of the assembled receptacle, cover member and hatch means showing the hatch means in the closed position and (in phantom) in the open position.

FIGS. 1 and 6 show a fully assembled container AA for storing a large number of pen needle assemblies. Container AA comprises a receptacle 10, a cover member 20 and hatch means 30.

The receptacle 10 is shown to be square-like in cross-section with sides 11, 12, 13 and 14 with a bottom 15. It will be understood that other cross-sections may be used such as the round cross-section of the container shown in FIG. 7. Another shape (not shown) would be. The receptacle is essentially an open cup with a top edge surface 10'. The receptacle is sized to hold up to a maximum pre-selected number of used pen needle assemblies.

The cover member 20 has a top portion and four sides: 22, 23, 24, and 25. As is clearly shown, the cover member 20 is sized to fit (snuggly) over the top of the receptacle 10. Latching or locking means may be used to lock the cover member to the receptacle; such means are shown in FIGS. 4 and 6 where the receptacle 10 has a radially extending shoulder 17 and the cover member has inwardly extending latch means 27 and shoulder means 26.

Figure 2:
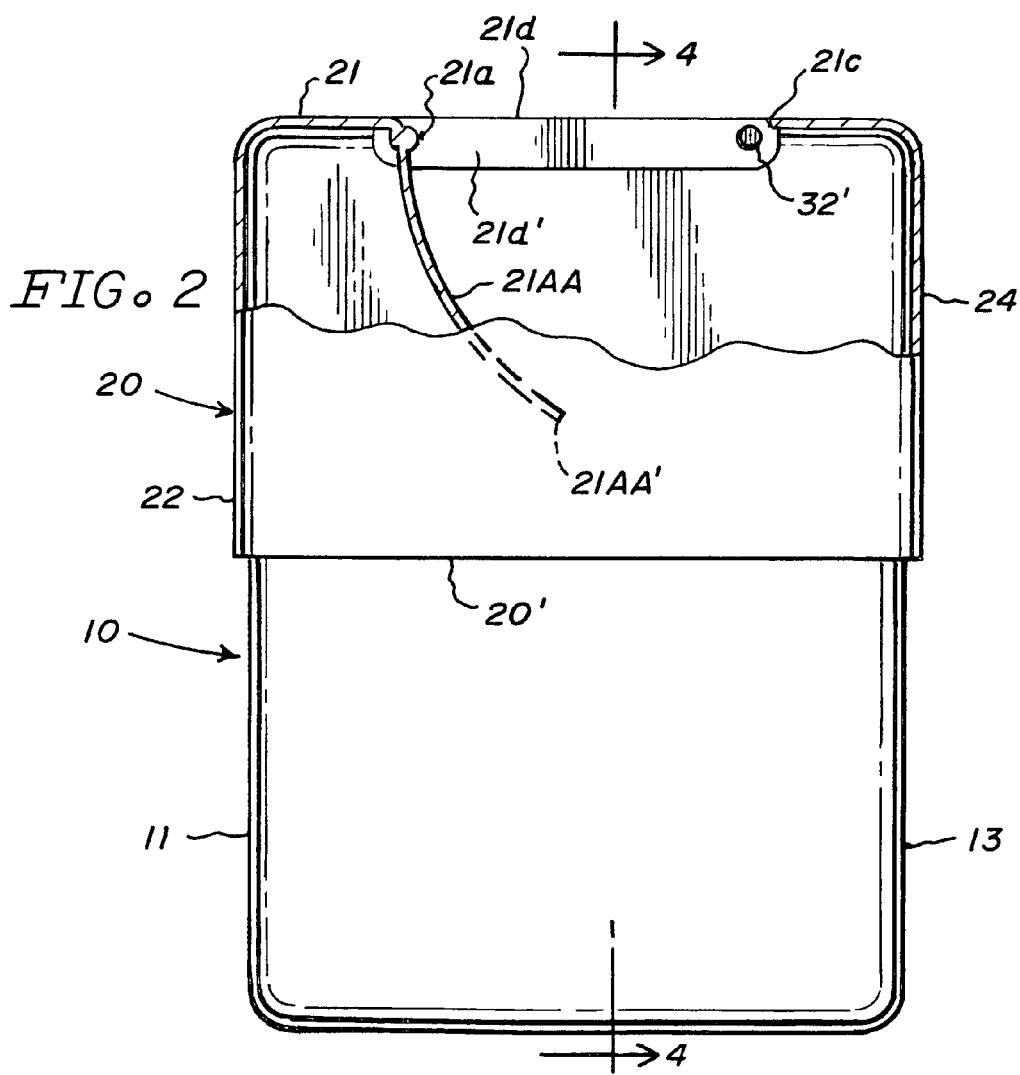
FIG. 2 is a cross-sectional view of the receptacle and attached cover member but excluding the hatch means.

The cover member 20 has a centrally located, square-shaped opening with sides 21a, 21b, 21c and 21d (see FIGS. 1, 2 and 4). Sides 21b and 21d have short, downward extending shoulders 21b' and 21d' as is best shown in FIG. 4. Side 21a has a rounded "cross-section" shape as is shown in FIG. 2.

Figure 3:
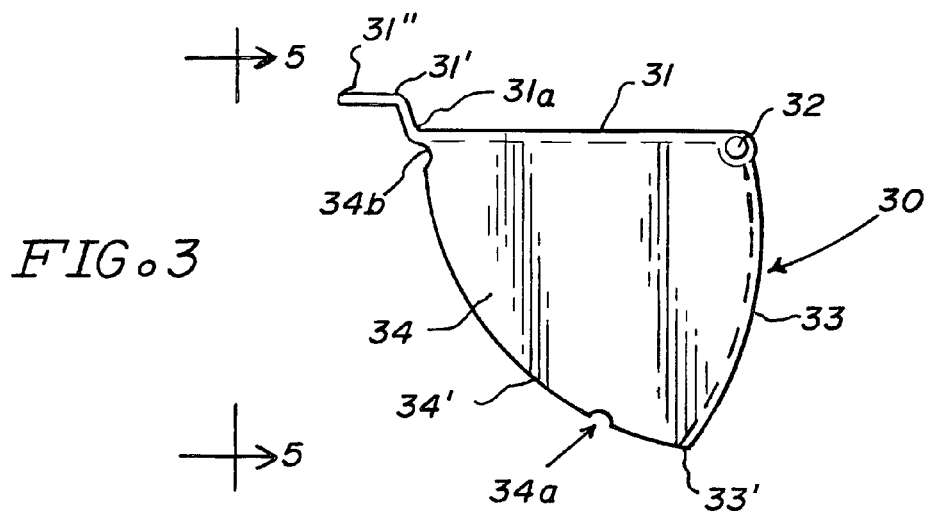
FIG. 3 is a right side view of the hatch means.

The hatch means 30 is positioned in the above described square-shaped opening and is supported by the cover member 20 for rotation between a closed position shown in FIG. 6 and an open position shown in FIG. 1. The hatch means comprises a square-shaped top portion 31 having a first end 31a from which depends an offset lip 31', the outboard edge 31" of which facilitates manual rotation of the hatch relative to the cover member 20. A pivot means is provided at the opposite end or side of the top portion 31; the pivot means are stub shaft elements 32 (see FIG. 5) which are fitted into bores 32' at the ends of shoulders 21b' and 21d' (see FIG. 2). The hatch means 30 also includes a bottom portion 33 which, in the preferred embodiment, has a curved shape as is best shown in FIGS. 3 and 6. The bottom portion 33 is integral with the pivot end of top portion 31 and the opposite end is identified by reference numeral 33'. The bottom portion has a lateral width substantially equal to that of the top portion. A pair of similar axially spaced-apart side portions 34 and 35 have a somewhat triangular shape (see FIG. 3 for 34) and are integral with top portion 31 and bottom portion 33. Further, the side portions have pre-selected curved edges 34' and 35'. The edges 34' and 35' in turn have notches 34a/34b and 35a/35b respectively for holding the hatch means in open and closed positions. The top, bottom and side portions of the hatch means collectively define a cup-like receiving means for receiving used pen needle assemblies as well as unprotected pen needles.

The container AA further includes a downwardly extending baffle means 21AA integral with the top surface 21 of cover member 20. Baffle means 21AA is an elongated, curved member attached at its top end (as shown in FIG. 2) to the underside of round edge or surface 21a of the opening in cover 20. The baffle means has approximately the same lateral width as that of the bottom portion 33 of the hatch means (see FIG. 1) and has a bottom, horizontally disposed edge 21AA' (see FIGS. 2 and 6).

As is best shown in FIG. 6, the curved edges 34' and 35' of the sides 34 and 35 of the hatch means 30 are sized to be in close, but not touching, contact with the curved baffle means 21AA.

Figure 7:
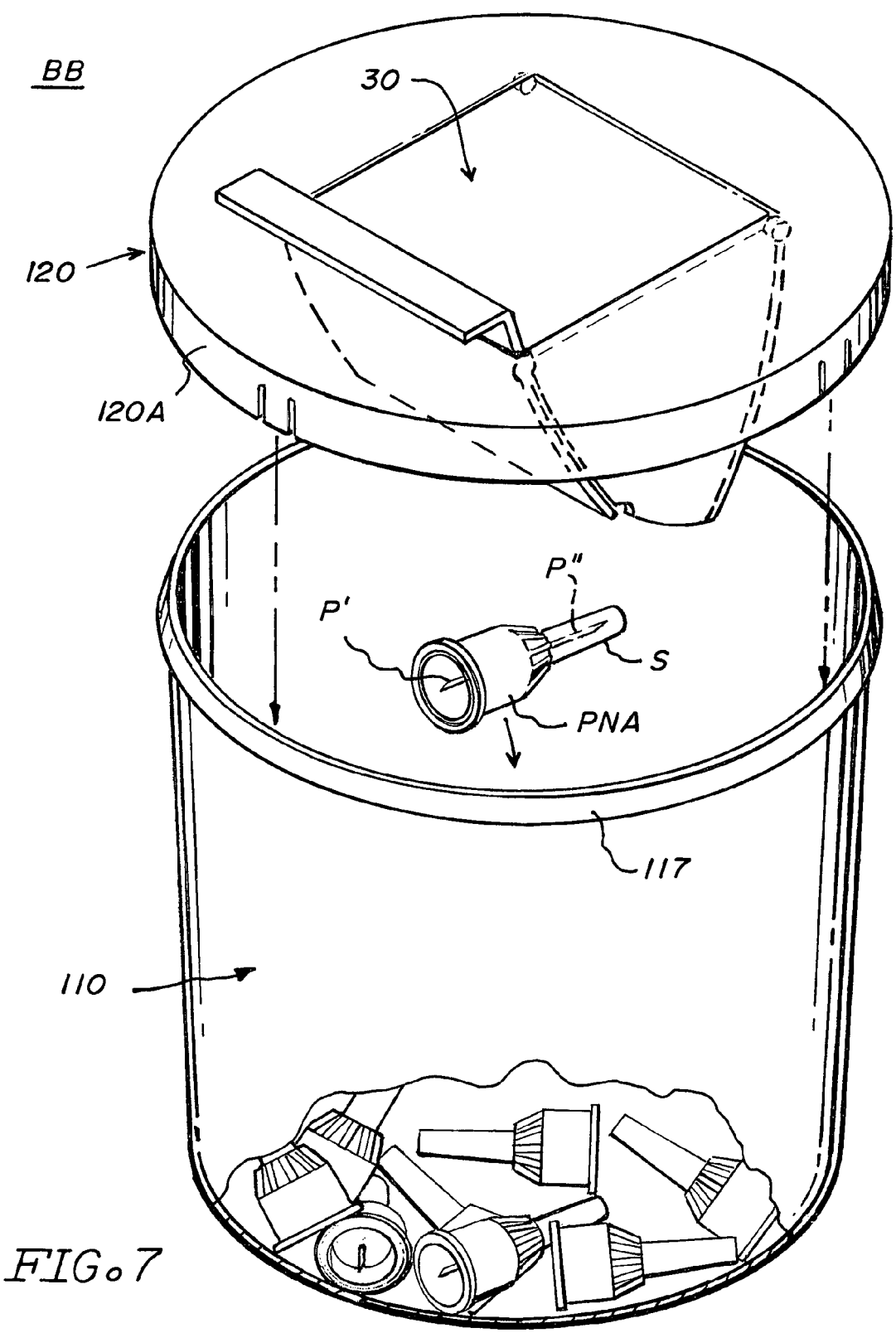
FIG. 7 shows another embodiment of the invention, a sharps container having a variation in the shapes of the receptacle and cover member.

The sharps container BB shown in FIG. 7 is very similar to that of FIGS. 1-6, except the receptacle and cover have a round cross-section. It comprises a receptacle 110, a cover member 120 with side means 120A and a hatch means 30 of the type above described. The receptacle 110 has a shoulder 117 for locking the cover member thereto. A representative PNA is shown in transit from the hatch means to the receptacle. A first end P' of the needle assembly is adapted to be received by the medical delivery pen as aforesaid; a second end P''' is protected by an outer shield S.

Operation

The user or pen needle assemblies (PNAs) can conveniently safely store used PNAs in the container AA. FIG. 6 shows a used PNA' ready to be stored. The hatch means 30 would be manually opened to the open position shown in FIG. 1 (also shown by dotted lines in FIG. 6). The hatch means would be held in said open position by the coaction between the notches 34a and 35a and the rounded surface 21a of the cover.

The said used PNA' then rests on the bottom portion 33 of the hatch means as is depicted (as PNA") in FIGS. 1 and 6. The hatch means is then manually rotated to the closed position shown in FIG. 6 and PNA" is released by the bottom portion 33 to slide, under the force of gravity, through the space between the edges 33' and 21AA' to the bottom of the receptacle 10 as PNA'''.

Of course, some users might not, for various reasons, re-insert the pen needle into its protective outer shield after the pen needle is disconnected from the medical delivery pen; for this scenario the container provided by this invention can be used to safely store the pen needles. Such unprotected pen needles may be placed onto the bottom portion of the hatch means and transferred into the receptacle 10.

An important feature of this invention is that the hatch means 30 permits only the transit of PNAs into the receptacle, but does not permit a used PNA or an unprotected pen needle to be removed from the receptacle, via the hatch means, once the same are in the receptacle. This is because the bottom portion 33 of the hatch means serves as a barrier when the hatch means is in the open position.

When the user of the sharps container wants to safely and hygienically dispose of used PNAs, the preferred procedure is to transfer the entire container to an approved disposal means or site without attempting to remove the cover from the receptacle.

While the preferred embodiment of the invention has been shown, it will be understood that variations may be made without departing from the inventive concept. It should, as an example, be understood that the term "pen needle assembly" (PNA) be interpreted to cover (i) a complete assembly including the above described cylindrical housing and axially extending needle with associated needle shield and outer shield, as well as (ii) the aforesaid assembly sans one or both shields.

Further, while the manually movable means which may be rotated between open and closed positions has been illustrated and described as hatch means 30, it will be under stood that other rotatable configurations are intended to be covered. Accordingly, the invention is to be limited only by the scope of the following claims.

The invention claimed is:

1. A container for storing a large number of used pen needle assemblies, said container comprising:
   a. an open-topped receptacle sized to hold a plurality of used pen needle assemblies;
   b. a cover member sized to fully cover said open-topped receptacle and including a top surface and a bottom surface; and
   c. a manually movable hatch means positioned in an opening in said top surface of said cover member, said hatch means comprising:
      (i) a top portion having a first edge thereof and pivot means spaced from said first edge, said pivot means being rotatably connected to said cover member and defining a rotational axis for rotation of said hatch means relative to said top surface of said cover member,
      (ii) a curved bottom portion, having a first edge thereof spaced from said pivot means, integral with said top portion and extending at a pre-selected angle relative to said top portion,
      (iii) axially spaced-apart side portions connected to said top and bottom portions, said top, bottom and side portions collectively defining a cup-like receiving means sized to receive only a single pen needle assembly; said hatch means being manually rotatable between a closed position whereat said top portion is substantially contiguous with said top surface of said cover member and an open position whereat said top portion is displaced with respect to said top surface of said cover member; and
   d. baffle means integral with said top surface of said cover member and extending at a pre-selected angle thereto, said baffle means having surface means substantially matching a pre-selected portion of said hatch means, and said baffle means being oriented and positioned with respect to said hatch means so, when said hatch means is rotated about said rotational axis, as aforesaid, to said open position, said baffle means and said pre-selected portion of said hatch means are in close proximity,
   wherein when said hatch means is in said open position, said bottom portion and side portions of said hatch means and a top portion of said baffle means cooperatively define four walls of a cavity below the top surface of the cover member sized to receive only a single pen needle assembly, further wherein when said hatch means is in the open position, said first edge of said curved bottom portion is positioned below the bottom surface of the cover member thereby exposing said top portion of said baffle means.

2. The container of claim 1 wherein said baffle means (i) is shaped with a pre-selected curved cross-section and (ii) terminates with a bottom baffle edge.

3. The container of claim 2 wherein said axially spaced-apart sides of said hatch means have similar outwardly extending edges, said edges being curved to be in close proximity with said pre-selected curved cross-section of said baffle means when said hatch means is in said open position.

4. The container of claim 3 wherein said bottom portion of said hatch means terminates with an edge defining a portion of said cup-like receiving means, said bottom baffle edge of said baffle means and said edge of said bottom portion of said hatch means being spaced apart a pre-selected distance when said hatch means is in said closed position, said pre-selected distance allowing the passage there-through of an used pen needle assembly.

5. The container of claim 4 wherein, when said hatch means is in said open position, said edge of said bottom portion of said hatch means is proximate said curved cross-section of said baffle means to thereby (i) facilitate a temporary resting area of an used pen needle on said bottom portion of said hatch means, and (ii) prevent removal of an used pen needle from said receptacle through said cover member.

6. The container of claim 1 including means for controlled holding of said hatch means in said open position.

7. The container of claim 6 wherein said means for controlled holding of said hatch means includes (i) means on said outwardly extending edges of said axially spaced-apart sides of said hatch means, and (ii) means on said top surface of said cover member.

8. The container of claim 1 including means for controlled holding of said hatch means in said closed position.

9. The container of claim 1 further characterized by said hatch means and said baffle means being sized so, when said hatch means is in said closed position, a pre-selected opening is defined between said hatch means and said baffle means to permit the free passage there-through of a used pen needle assembly.

10. The container of claim 1 further characterized by said including means connected to said first edge of said top portion of said hatch means to facilitate said manual rotation of said hatch means between said open and closed positions.

11. The container of claim 1 further including means on said receptacle and said cover member for locking said cover member to said receptacle.

12. The container of claim 1 wherein the top portion of the hatch means is longer than the curved bottom portion.

13. The container of claim 1, wherein when the hatch means is in the open position, the cavity has an accessible top opening having substantially the same area as the bottom portion of the hatch means.

* * * * *